(12) United States Patent
Freedland

(10) Patent No.: US 6,270,304 B1
(45) Date of Patent: *Aug. 7, 2001

(54) TENSION ADJUSTING DEVICE

(76) Inventor: Yosef Freedland, The 93 Street #10/7, Petah Tikvah (IL), 49312

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/184,121

(22) Filed: Jan. 21, 1994

Related U.S. Application Data

(63) Continuation-in-part of application No. 08/034,269, filed on Mar. 23, 1993, now abandoned.

(51) Int. Cl.[7] .............................. F16B 23/00; F16B 35/00
(52) U.S. Cl. ...................... 411/392; 411/366.1; 411/400; 606/73
(58) Field of Search .................................... 411/366, 367, 411/392, 400, 432, 533, 366.1, 368; 606/63, 73

(56) References Cited

U.S. PATENT DOCUMENTS

| | | | |
|---|---|---|---|
| 826,131 | * 7/1906 | Weaver | 411/392 |
| 1,963,514 | * 6/1934 | Wherren | 411/400 X |
| 2,017,114 | * 10/1935 | Winchester | 411/155 X |
| 2,625,357 | * 1/1953 | Atkinson | 411/400 |
| 4,589,179 | * 5/1986 | Hulting, Jr. | 411/392 X |

* cited by examiner

*Primary Examiner*—Neill Wilson
(74) *Attorney, Agent, or Firm*—Rick Matos; Innovar, L.L.C.

(57) ABSTRACT

The invention provides an improved Winged Fastener in which a large threaded nut is movably engaged with the threaded sleeve of the Winged Fastener wherein the nut is movable set in a washer such that the washer is placed against a surface, while the sleeve of the winged bolt is placed in a bore in a first matrix and a second matrix is set around the sleeve of the Winged Bolt. As the nut is turned on the threaded sleeve, the second matrix which is placed around the threaded sleeve is caused to be compressed and radially moved outward toward an inner surface of the first matrix. If the second matrix is of a rigid material, the cylinder of matrix is split longitudinally and the pieces are driven radially outward.

The invention also provides a second improved Winged Fastener in which a hole is placed in a wing and a cable or tendon is attached to the wing through the hole. The threaded shaft of the Winged Fastener is placed in a threaded nut which is movably set in a washer such that the washer is placed against a matrix and the shaft and wings of the winged bolt are placed in a bore through the matrix. The opposite end of the cable or tendon is anchored deep in the bore and as the nut is turned around the threaded shaft, the Winged Bolt is retracted into the nut and tension is placed on the cable.

4 Claims, 3 Drawing Sheets

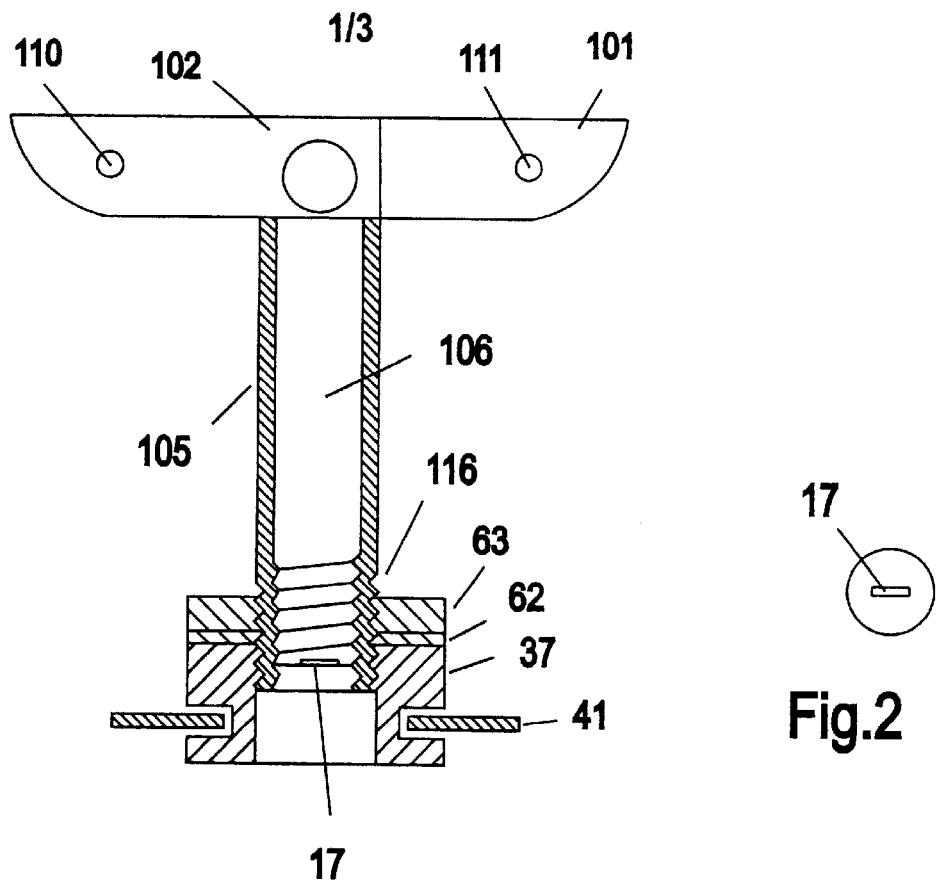
Fig.1
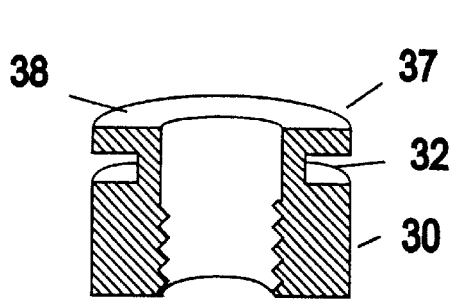
Fig.2
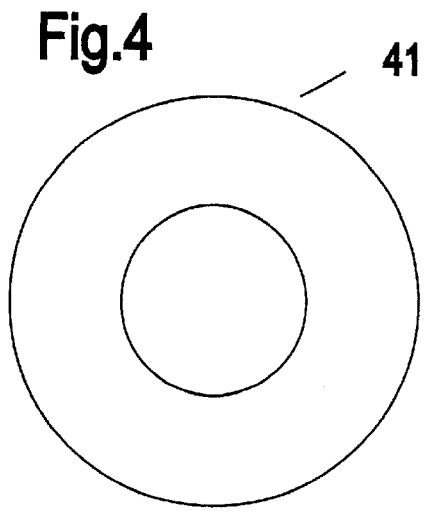
Fig.3
Fig.4

FIG. 5
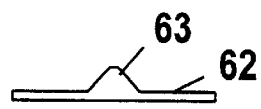
FIG. 6
FIG. 8
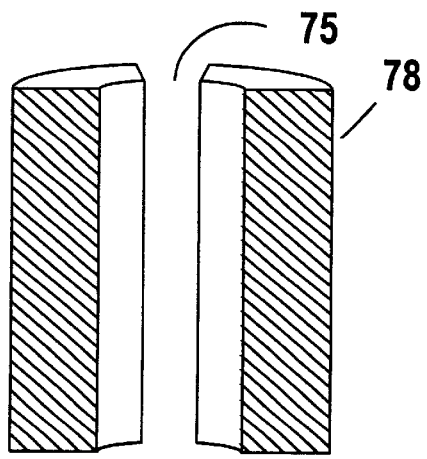
FIG. 7
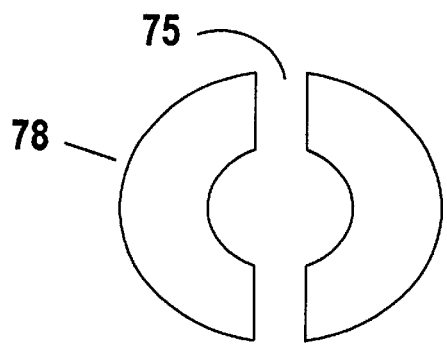
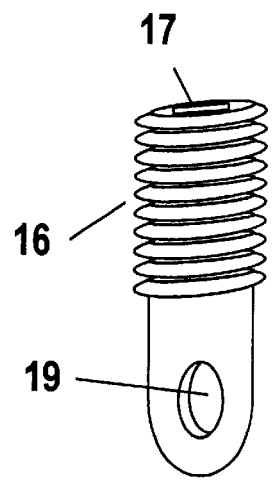
FIG. 9

TENSION ADJUSTING DEVICE

CROSS-REFERENCE TO EARLIER FILED APPLICATION

The present application is a continuation-in-part of U.S. patent application Ser. No. 08/034,269 filed Mar. 23, 1993.

FIELD OF THE INVENTION

The present invention relates to devices used to secure flexible material to concrete substrate such as cable to a wall, or tendon to bone. The present invention relates to a method, and a screw device therefor, for tensioning a cable such that rotation of the cable is prevented when the screw is turned.

BACKGROUND OF THE INVENTION

Various fasteners have been described which provide compression to a surface. Standard screws provide an anchoring of the screw through the shear force exerted by the thread against the walls of the bore in which it is embedded. The head of the screw provides compression against the material. In situations where threads cannot purchase the material surrounding the bore, jackets surrounding the threads of the screw are often utilized. The jacket is designed to expand in the bore of the material and provide anchoring for the screw threads. Known screw devices cannot deliver a precise level of load to the cable or tendon tension. At present, when a cable is attached to a screw, or a sheath around the screw, and the screw is turned, the cable or sheath are not stabilized against rotation with respect to the substrate to which the screw is engaged One type of known compressive bolt device consists of wings which provide compression to a surface of the material in which the device is mounted. Thus both sides of the bolt are compressing material as opposed to screws where one side is acting in shear. These devices generally are not wholly removable and require the wing side of the device to be left within or on the surface of the material within which the device was installed, when the bolt portion is removed.

Another type of known compressive bolt device includes winged bolts in which the device is wholly removable following use. Some of these devices are disclosed in U.S. Pat. No. 4,409,974 issued in 1983, which covers a bone-fixating surgical implant device.

SUMMARY OF THE INVENTION

The present device both provides a compression anchor and permits precise adjustment of the tension of an attached tendon or cable while preventing the tendon or cable from turning with appropriate instrumentation. The present device comprises an outer nut and an inner bolt to which a cable or tendon can be attached. By rotating the outer nut, the inner bolt is retracted in or out of the nut and hence tightening or loosening the cable or outer sheath.

The present invention provides a fixation device for bringing one object close to another by applying a compressive force on one or more surfaces of the objects being brought closer together. One end of the device is attached to a cable which is anchored in a second surface. One embodiment of the invention employs a sheath mounted around the shaft of a screw such that when the device is installed, the sheath is caused to expand radially outward as the screw is tightened.

Another embodiment of the device has a cylindrical inner shaft surrounded by a cylindrical sleeve, with a washer around the cylindrical sleeve. The inner shaft ends in an eyelet adapted to receive a cable or tendon. This device has slots in the end of the device, both on the inner shaft and on the outer nut, to receive a tool that can insert and deploy the bolt.

Yet another embodiment of this device employs a sheath surrounding a screw, an outer nut at one end of the screw, and a washer at the end of the screw, opposite the outer nut, such that by turning the outer nut the screw is brought closer to or further from the nut. In this way, the sheath of material is caused to expand radially outwardly from the screw. The sheath can be made of a single piece rigid material or a solid material. In the case of a solid material, there are longitudinal cuts in the sheath such that the longitudinal pieces can expand outwardly.

Still another embodiment of this device utilizes the Winged Compression Bolt disclosed in U.S. Pat. No. 5,098,433, which device comprises an outer sleeve surrounding a central screw and an outer nut threaded onto the outer sleeve. Turning the outer nut around the outer sleeve such that the wings of the device are pulled inward or outward from the nut, causing the outer sleeve, or sheath, to push radially outward on surrounding material. Holes in the wings will allow for a cable or tendon to be attached to the wings. When the other end of the cable or tendon is attached to second object, the cable or tendon can be loosened or tightened by turning the outer nut.

It has been discovered according to the present invention that because the nut can be rotated in increments, the cable or tendon can be adjusted in tension to a precise degree such that the cable attached to the end of the screw or the sheath put around the screw will be able to be put under tension or compression, respectively, to a precise degree.

It has also been discovered according to the present invention that by using a cylindrical sheath, which is split longitudinally, along with a washer having a ridge on it, the sheath can be caused to push radially outward in a uniform fashion when the nut is tightened about the screw.

It has also been discovered according to the present invention that if the sheath around the sleeve is made of a soft material, the sheath can be of a single piece and made to expand uniformly outward from the threaded shaft when the nut is tightened about the screw.

It has also been discovered according to this invention that the tools which deploy the nut and screw can stabilize the inner screw and rotate the outer nut.

It is therefore an object of this invention to provide an apparatus having a sheath which creates a compressive force on an area of surrounding material with a sheath around its shaft or as a result of creating a tensile force on a tendon or cable attached to an end of the shaft such that the device will maintain the surrounding material in a steady, non-rotating manner while compressing or loosening the material.

It is further an object of this invention to provide a fixation device that is removable from the hole when it is desired to be removed.

Accordingly, the present invention provides a tension adjusting device for creating tension on material comprising:
  a. a hollow outer nut (sleeve) having a sidewall enclosing a centrally disposed opening within the nut, a front end and a rear end;
  b. an elongated shaft having a first end and a second end, which shaft is movable and within the opening in the hollow outer nut;
  wherein the mean length of the device is adjusted by changing the relationship outer nut and elongated shaft.

Some preferred embodiments of the invention include those wherein: 1) the hollow outer nut is rotatable around the elongated shaft; 2) the shaft is threaded and has a slot at one end; 3) the nut comprises an internally threaded cylinder; 3) the elongated shaft is threaded and has a flat surface on it by which it can be engaged to stabilize it while the nut is rotated about it; 4) the elongated shaft has hole or securing coupling at an end to allow it to attach a material which requires anchoring; 5) the outer nut is rotatable while the inner elongated shaft is stabilized thereby causing the inner shaft to move within the sleeve such that any material attached to the shaft can be tightened; 6) the device comprises an inner sleeve and the outer nut is movable against the inner sleeve such that the sleeve is more or less contained within the outer nut; 7) the elongated shaft is threaded and has a slot at the first end and further comprises a washer or "O" ring at the opposite second end, wherein the washer or "O" ring is rotatably engaged with the shaft so as to provide compression on a material; 8) the device further comprises a first grooved nut below an "O" ring at the first end of the shaft and a second grooved nut is placed on a surface of the nut such that the grooves are facing each other; 9) a cylinder of material is placed between the ends of the device; 10) a split cylinder of material is placed between two "O" rings onto which grooved washers have been placed such that the cylinder can split and expand radially outward along the length of the cylinder; 11) the elongated shaft is a winged compression bolt; 12) the elongated shaft is a winged compression bolt, a cylinder of material is placed around a sleeve of the compression bolt, and a grooved washer is placed near the outer nut; and 13) the elongated shaft is a winged compression bolt, a cylinder of material is placed around the compression bolt, and a grooved washer is placed near the outer nut, wherein the cylinder is caused to expand radially outward when the outer nut is rotated and the compression bolt is held stable.

Another aspect of the invention provides a method of tensioning a cable or tendon by drilling a bore in a matrix and attaching the tendon or cable to a second matrix at a far point in the bore and the other side of the cable or tendon to the end of a threaded shaft. A nut is placed around the threaded shaft and a movable washer is placed around the nut such that it makes contact with the surface of the matrix into which the bore has been drilled. By turning the nut which is rotatably attached to the washer, the cable or tendon is tightened in a manner such that the cable or tendon is maintained in a stable, non-rotating fashion during this process, putting tension on the cable or tendon.

Still another aspect of the invention provides a method for plugging a hole in a single material or a hole straddling two separate materials by drilling a bore in the material or obliquely or lengthwise to the interface of the two materials such that the bore straddles the two materials. A threaded shaft with a nut and washer at one end and a washer at the other end and a matrix sheath surrounding the threaded shaft is placed in the bore and the nut is turned, compressing the matrix radially outward into the walls of the bore in the substance, creating a compressive contact along the length of the bore between the walls of the bore and the inserted matrix.

Yet another aspect of the invention provides a method for plugging a hole in a single material or a hole straddling two separate materials by drilling a bore in the material or obliquely or lengthwise drilling a bore such that it straddles the two materials. A rigid matrix with longitudinal splits is put around a threaded shaft. At one end there is a nut with a washer arrangement and at the other end there is a washer or perpendicularly deployed wings. At the nut end or at both the nut end and the opposite end, a washer with a ridge is placed such that the ridge interfaces with the split in the matrix jacket. The threaded shaft, and matrix material is put into the bore in the bone and the washer is set around the nut on the surface of the bore. The nut is turned, causing the matrix to separate along the splits and move radially outward toward the walls of the bore.

Still yet another aspect of the invention provides a method for both plugging a bore within a single matrix or across two matrices while putting tension on a cable or tendon such that a hole is bored into the single matrix or along the interface of the two matrices or obliquely to the two matrices. A cable or tendon is attached to another surface at a distant part of the bore or deep within the bore and its second end is attached to a threaded shaft with a hole in its end or in its perpendicular wing. Around the threaded shaft is a third matrix which is either a single cylinder or a cylinder which has been cut longitudinally. At one end of the threaded shaft, below the holes is a movable washer. At the other end is a nut which is set in a moveable washer. The threaded shaft and the third matrix is placed in the bore with the washer against the surface of the third matrix around the bore and the nut is turned. This causes retraction of the cable or tendon creating tension on it while at the same time, causing the third matrix around the threaded shaft to be forced radially outward into the surrounding bore which is in the single matrix or two matrices.

BRIEF DESCRIPTION OF THE DRAWINGS

Referring particularly to the drawings for the purpose of illustration only and not limitation:

FIG. 1 depicts a sectional side view of the Winged Compression in the deployed position with a nut and washer around the sleeve. The washer is embedded in a groove in the outer nut.

FIG. 2 depicts an end-on view of the upper end of the shaft of the Tension Adjusting Device of FIG. 9.

FIG. 3 is a cross-sectional perspective view of the outer threaded nut of the Tension Adjusting Device wherein the nut has a circumferential groove in order to receive the washer.

FIG. 4 depicts a top plan view of the "O" ring which fits in the groove of the nut of the Tension Adusting Device.

FIG. 5 depicts a side view of a washer having a ridge running its length. The washer is used to apply radially outward pressure on a matrix around the shaft.

FIG. 6 depicts a side view of the washer of FIG. 5 rotated 90 degrees so that the ridge can be viewed.

FIG. 7 depicts a cross-sectional side view of the outer sheath which is placed around the outer sleeve of the Winged compression Bolt in FIG. 1.

FIG. 8 depicts a top plan view of the sheath of FIG. 7 having two halves.

FIG. 9 depicts a perspective of the central threaded piece which is part of the nut assembly of FIG. 10.

DETAILED DESCRIPTION OF THE INVENTION

Although specific embodiments of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit and scope of the invention as further defined in the appended claims.

Many materials will not hold conventional screws well. This is because the materials have poor shear strength. An exemplary material is plaster board. When a screw is put into plaster board, the plaster tends to crumble under any amount of pullout power. On the other hand, the surface compressive strength of plaster board is relatively good. A washer or button on the surface of the plaster boards spreads the load over a larger area.

The present invention provides a Tension Adjusting Device with compressive fixation forces that improves on known button anchors in that the tension can be adjusted without twisting the cable which is attached to it or without twisting the outer sheath which is used to push against the walls of the bore in the material in which the device is placed.

Figure 10:
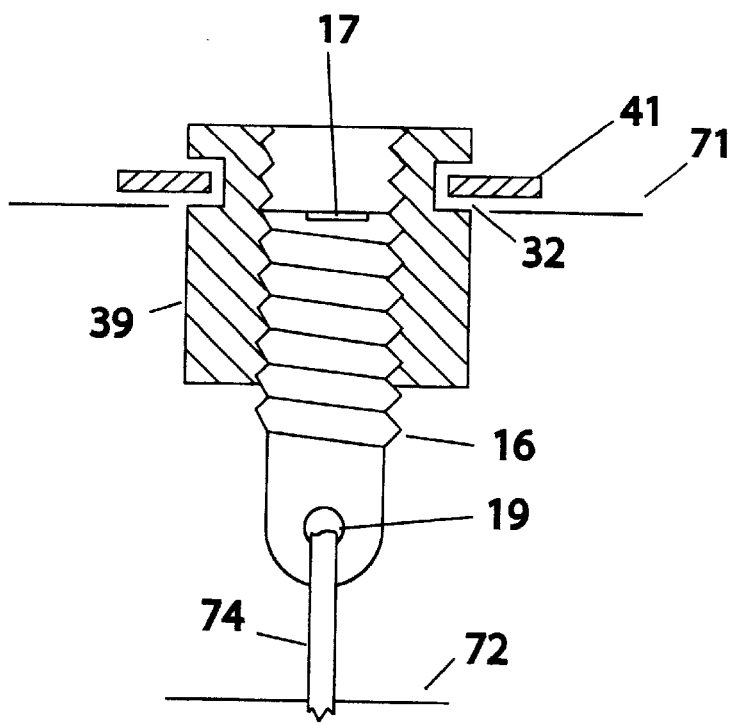
FIG. 10 depicts a partial sectional side view of the assembled tension adjusting device which is used to adjust the tension of an engaged cable in order to put the cable under greater tension or to loosen the tension on it.

FIG. 10 shows this cable-pulling device in its fullest form. The outer threaded nut has notch 32 in it for the "O" ring, 41 and has a hexed 37 outer configuration, as seen in FIG. 3. This configuration could be varied in that the slot 17 could be a hex or phillips slot. The threaded shaft 16 has screw slot 17 in it and cable hole 19 in its opposite end. By applying a hex wrench or other similarly coupled instrument to the outer sleeve 30, and turning the outer hex wrench while the inner shaft 16 is stabilized by a screwdriver or similar stabilizing device in slot 17, the inner shaft 16 can be either screwed into the outer nut 30 or away from it, giving precise tension on the cable which is attached to the ring 19 in the end of the inner shaft 16.

Figure 11:
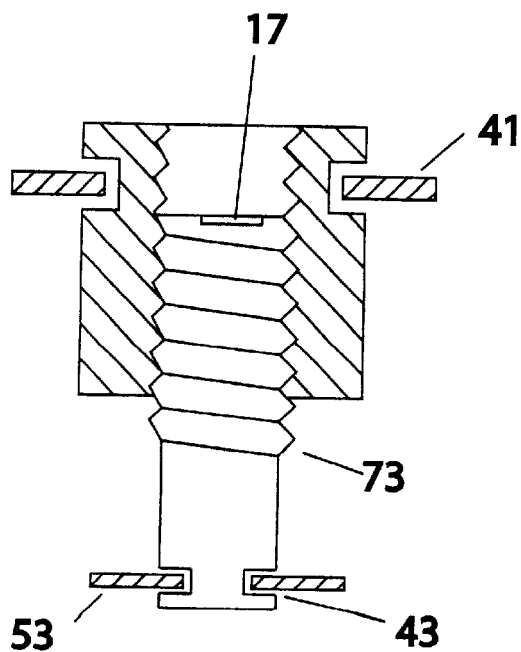
FIG. 11 depicts a partial sectional side view of a tension adjusting device in which the central thread piece of FIG. 9 has a washer placed at its end. This allows the device to be used with a sheath, such as in the one depicted in FIG. 7. In use, the washer will cause the sheath to expand outward in a radial fashion.

Another embodiment of the same concept is shown in FIG. 11 in, at the end of the inner shaft 16, there is a notch 43 to receive an "O" ring 53. Between the "O" ring 53 and "O" ring notch 43, a soft cylinder of material, such as a cylinder 78, of rubber or bone shown in FIG. 7 which can be totally circumferentially enjoined or split along line 75 can be placed. By putting the cylinder, 78, around the threaded sleeve 73 and turning the outer nut 37 on the inner sleeve 73 while the inner sleeve is stabilized at slot 17, the material 78 between the "O" rings, 41 and 53 can be compressed or decompressed in a precise manner.

In the embodiment of FIG. 11, a washer 62, with a ridge 63 on it, as depicted in FIG. 6 and FIG. 5, can be placed below the "O" ring 41 and another washer 62 can placed above the "O" ring 53 such that the two ridges face each other. These ridges fit between the pieces of the cylinder 78 such that as the ridges are pushed toward each other, the cylinder pieces are caused to expand outwardly.

When a ligament or cable 74 is attached to the end 41, as depicted in FIG. 10, and the opposite end of the ligament or cable 74 is anchored into a matrix 72 such as bone, rotating the outer nut 30 on the inner shaft, while the "O" ring is maintained against a surface 71, will adjust the tension on the cable or ligament 74 without causing the cable or ligament to rotate at all or, depending upon the rigidity of the tendon or cable to prevent rotation of the ligament or cable during the rotation of the outer sleeve.

An alternate embodiment of this device is displayed in FIG. 1 in which the Winged Compression Bolt has been installed so that the wings, 101 and 102 have been deployed as described in U.S. Pat. No. 5,098,433, issued Mar. 21, 1993. The wing 101, 102 rest on the outer sleeve 105, and the outer nut 37 is shown in place with the "O" ring 41 around it. On top of the outer nut, 37, the washer 62 with ridge 63 is placed such that the ridge 63 is facing and aligned with the upper wings, 101 and 102. By putting a screwdriver in the slot 17, the threads 116 can be stabilized while the outer nut 37 is turned, bringing the wings towards the nut 37.

Alternatively, a cable or tendon is threaded through either hole 111 or 110 in the wings 101 or 102 or through both. As the outer nut, 37, is turned, the washer, 41 is kept stationary against the outer bore of the matrix and the threaded shaft 106 is also maintained stationary by way of a tool inserted in slot 17 so that the shaft 106 can be brought into or away from the nut, 37 thereby tensioning or slackening the cable which has been attached to either hole 110 or 111 or both and anchored at some distant point deeper in the bore in the matrix. In this embodiment, washer, 62, is not necessary unless a cylindrical matrix is placed around the shaft 16 at the same time.

What is claimed is:

1. A device for adjusting the tension on a cable by applying a compression force to an anchor surface of a matrix, said device including:

a compression member having a body and a threaded bore therethrough, said body having at least one compression surface for applying said compression fixation force to said anchor surface of said matrix; and a shaft having a threaded portion at one end for mating with said threaded bore and further having a receptacle at the other end thereof for receiving said cable to be tensioned; said compression member being adapted to be rotated around said shaft while said shaft is adapted to be stabilized against rotation to prevent torsion of said cable, wherein said cable is a tendon or ligament.

2. A device for adjusting the tension on a cable by applying a compression force to an anchor surface of a matrix, said device including:

a compression member having a body and a threaded bore therethrough, said body having at least one compression surface for applying said compression fixation force to said anchor surface of said matrix; and a shaft having a threaded portion at one end for mating with said threaded bore and further having a receptacle at the other end thereof for receiving said cable to be tensioned; said compression member being adapted to be rotated around said shaft is adapted to be stabilized against rotation to prevent torsion of said cable, wherein said matrix is bone.

3. A method for adjusting the tension on a cable including the following steps:

applying a compressive fixation force to an anchor surface of a matrix, using a compression member having a body and threaded bore therethrough and at least one compression surface for applying said compression fixation force to said anchor surface and a shaft having a threaded portion at one end thereof for mating with said threaded bore and further having a receptacle at the other end thereof for receiving the cable:

attaching the cable to said receptacle;

stabilizing the shaft against rotation to prevent torsion of said cable; and rotating the compression member around said shaft, wherein said cable is a tendon.

4. A method for adjusting the tension on a cable including the following steps:

applying a compressive fixation force to an anchor surface of a matrix, using a compression member having a body and threaded bore therethrough and at least one compression surface for applying said compression fixation force to said anchor surface and a shaft having a threaded portion at one end thereof for mating with said threaded bore and further having a receptacle at the other end thereof for receiving the cable:

attaching the cable to said receptacle;

stabilizing the shaft against rotation to prevent torsion of said cable; and rotating the compression member around said shaft, wherein said matrix is bone.

* * * * *